United States Patent
Abdel-Rahman

(10) Patent No.: US 11,952,326 B1
(45) Date of Patent: Apr. 9, 2024

(54) PHOTOSWITCHABLE ISOMERIZATION OF STERICALLY HINDERED 2,2',6,6'-TETRA-ISOPROPYL-4,4'-DIETHYNYLAZOBENZENE

(71) Applicant: KING FAISAL UNIVERSITY, Al-Ahsa (SA)

(72) Inventor: Obadah Subhi Abdel-Rahman, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/540,206

(22) Filed: Dec. 14, 2023

(51) Int. Cl.
  *C07C 245/12* (2006.01)

(52) U.S. Cl.
  CPC .................. *C07C 245/12* (2013.01)

(58) Field of Classification Search
  CPC .................................................. C07C 245/12
  See application file for complete search history.

(56) References Cited

U.S. PATENT DOCUMENTS

| 4,248,678 A | 2/1981 | Goodin et al. |
| 4,293,392 A | 10/1981 | Hallcher et al. |
| 4,293,393 A | 10/1981 | Hallcher et al. |

FOREIGN PATENT DOCUMENTS

JP   2013095685 A   5/2013

OTHER PUBLICATIONS

Al-Balushi et al., Inorganic Chemistry (2016), 55(21), 10955-10967. (Year: 2016).*
PubChem 10 most similar relevant structures to applicants PA0001171, 2005.
Bisle, et al. "Fluorescence of noncyclic azo compounds with a low-lying 1 (n, π*) state." Chemical Physics Letters 31.2 (1975): 264-266, Abstract only.
Forber, et al. "Electronic spectra of cis-and trans-azobenzenes: consequences of ortho substitution" Journal of the American Chemical Society 107.21 (1985): 5884-5890.

* cited by examiner

*Primary Examiner* — Laura L Stockton
(74) *Attorney, Agent, or Firm* — Nath, Goldberg & Meyer; Richard C. Litman

(57) ABSTRACT

A reversible photo-switchable isomerization of novel sterically hindered 2,2',6,6'-tetraisopropyl-4,4'-diethynylazobenzene and its synthesis.

8 Claims, 2 Drawing Sheets

PHOTOSWITCHABLE ISOMERIZATION OF STERICALLY HINDERED 2,2',6,6'- TETRAISOPROPYL-4,4'-DIETHYNYLAZOBENZENE

BACKGROUND

1. Field

The present disclosure relates to a compound that is a sterically hindered 2,2',6,6'-tetraisopropyl-4,4'-diethynylazobenzene, its photoswitchable isomerization, and its synthesis.

2. Description of the Related Art

Azoarylene (also known as diazene or diimide) derivatives are reversible photo switchable chemical compounds composed of two aryl rings linked by a N═N double bond which can change their structural geometry and chemical properties upon irradiation with electromagnetic radiation. Those reversible photoswitchable compounds have been intensively investigated and attracted enormous interests to clarify the mechanism of cis-ltrans-isomerization and to understand their applications utilizing alteration of the chemical structures in terms of photoswitching and high-density information optical storage devices.

Azoarylenes are highly accessible through a straightforward step of classical homo-oxidative cross-coupling of aryl diazonium salts using Cu-catalyzed Sandmeyer-style reaction. The products of orange chromophores usually show a remarkably strong $\pi \rightarrow \pi^*$ transition in the visible (Vis) regime of the electromagnetic radiation which can be predictively tuned by introducing substituents on the aryl rings.

Azoarylenes generally undergo an ultraviolet (UV) light ($\lambda \approx 340–380$ nm)–triggered transition from thermally stable apolar trans-form to polar cis-configuration with a bent conformation (dipole moment of about 3.1 Debye). On other hand, storing azoarylenes in the dark or under visible light of the electromagnetic radiation ($\lambda \approx 420–490$ nm) will reverse the transition process. Trans-azoarylens are planar compound with a N═N distance of about 1.195 Å, while the cis-azobenzenes are non-planar with a C—N═N—C dihedral angle of about 175.2°.

SUMMARY

The present compound is a photo switchable isomerization of novel sterically hindered 2,2',6,6'-tetraisopropyl-4,4'-diethynylazobenzene with four bulky isopropyl groups on the ortho-positions. The compound was synthesized via subsequent desilylation of the two protecting Me₃Si (TMS) groups of 2,2',6,6'-tetraisopropyl-4,4'-bis((trimethylsilyl) ethynyl)azobenzene according to classical procedure.

The identity of this novel sterically hindrance compound follows the correct numbers and integrations of its ¹H-NMR data. ¹H-NMR spectrum, shows a singlet of the four aromatic equivalent protons at δ=7.13 ppm, another singlet observed at δ=3.24 ppm for the two equivalent terminal ethynyl protons and classical heptet at δ=2.86 ppm and doublet at δ=1.25 ppm for the methine CH(CH₃)₂ and methyl (CH₃)₂CH protons of the four equivalent isopropyl groups, respectively.

In an embodiment, the present subject matter relates to a sterically hindered 2,2',6,6'-tetraisopropyl-4,4'-diethynylazobenzene complex having the formula I:

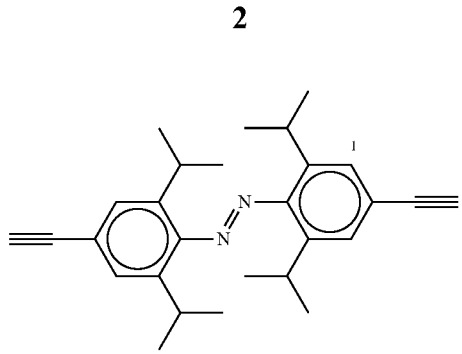

In a further embodiment, the present subject matter relates to a compound that may be switched between trans- and -cis isomers by irradiation of electromagnetic radiation.

In one more embodiment, the present subject matter relates to a method of making the sterically hindered 2,2', 6,6'-tetraisopropyl-4,4'-diethynylazobenzene, the method comprising: dissolving 2,2',6,6'-tetraisopropyl-4,4'-bis ((trimethylsilyl)ethynyl)azobenzene, in a methanol and tetrahydrofuran (THF) mixture to obtain a reaction mixture; adding potassium carbonate to the reaction mixture; evaporating the methanol and tetrahydrofuran (THF) from the reaction mixture to obtain a crude residue; dissolving the crude residue in a mixture of CH₂Cl₂ and water to obtain an organic layer; extracting and drying the organic layer; removing the mixture of CH₂Cl₂ and water; and obtaining the sterically hindered 2,2',6,6'-tetraisopropyl-4,4'-diethynylazobenzene.

These and other features of the present subject matter will become readily apparent upon further review of the following specification.

DETAILED DESCRIPTION OF THE PREFERRED EMBODIMENTS

Figure 1:
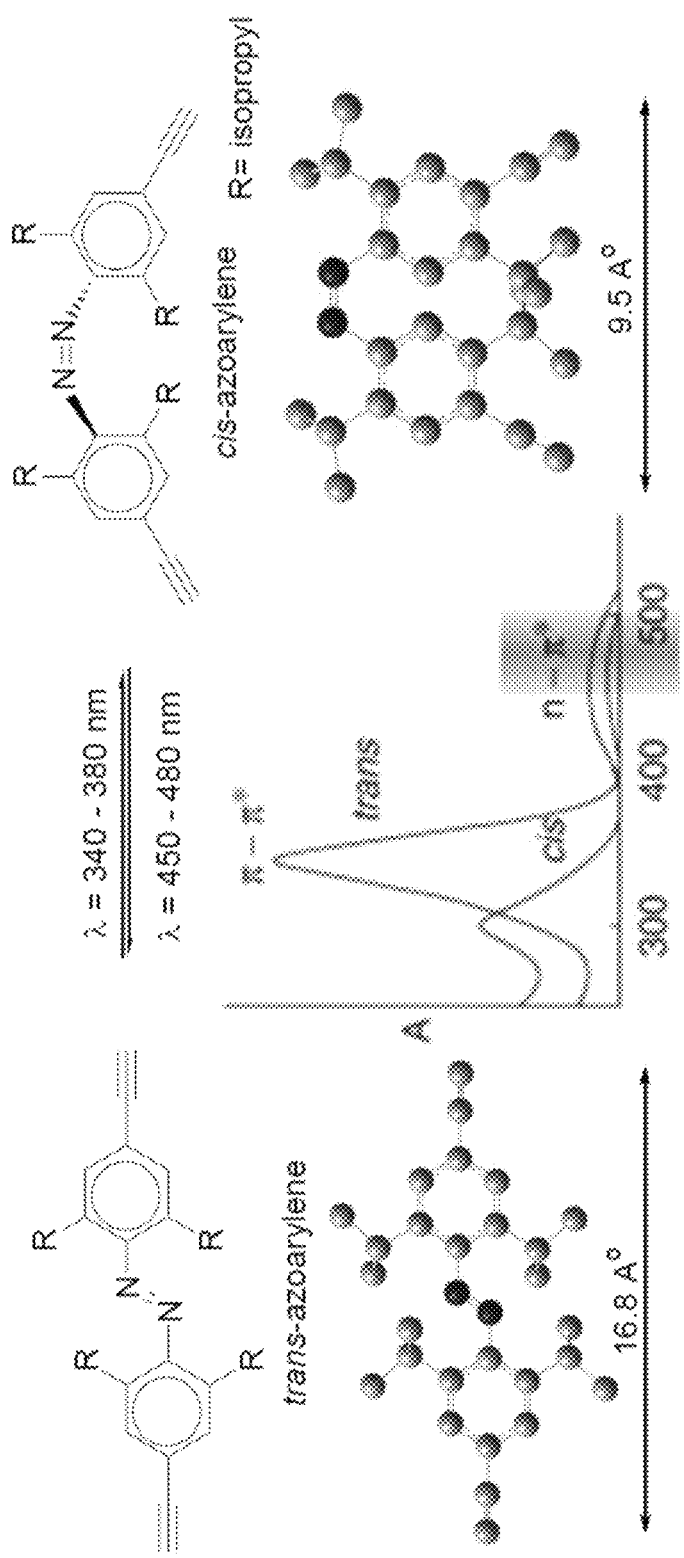
FIG. 1 shows a reversible photo switchable isomerization of sterically hindered 2,2',6,6'-tetraisopropyl-4,4'-diethynylazobenzene.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to novel photoswitchable isomerization of novel sterically hindrance 2,2',6,6'-tetraisopropyl-4,4'-diethynylazobenzene with four bulky isopropyl groups on the ortho-positions via subsequent desilylation of the two protecting $Me_3Si$ (TMS) groups of 2,2',6,6'-tetraisopropyl-4,4'-bis((trimethylsilyl)ethynyl) azobenzene according to classical procedure. This compound is a chromophore and shows a remarkably strong $\pi \rightarrow \pi^*$ transition in the Visible (Vis) regime and undergoes photoswitching of trans- and cis-isomers which is highly controlled by irradiation of electromagnetic radiation.

The identity of this novel sterically hindered compound follows the correct numbers and integrations of its $^1$H-NMR data. $^1$H-NMR spectrum shows a singlet of the four aromatic equivalent protons at δ=7.13 ppm, another singlet observed at δ=3.24 ppm for the two TMS protecting groups and heptet at δ=2.86 ppm and doublet at δ=1.25 ppm for the methine $CH(CH_3)_2$ and methyl $(CH_3)_2CH$ protons of the four equivalent isopropyl groups, respectively.

In an embodiment, the present subject matter relates to a sterically hindered 2,2',6,6'-tetraisopropyl-4,4'-diethynylazobenzene having the formula I:

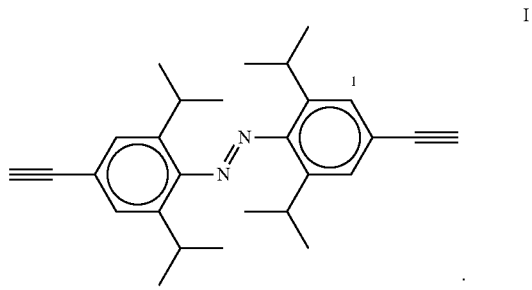

I

In another embodiment, the present subject matter relates to a photo switchable compound between trans- and -cis isomers by irradiation of electromagnetic radiation.

In one more embodiment, the photo switchable application may be useful in high-density information optical storage devices.

The present subject matter relates to a method of making the sterically hindered 2,2',6,6'-tetraisopropyl-4,4'-diethynylazobenzene with four bulky isopropyl groups on the ortho-positions was successfully prepared via subsequent desilylation of the two protecting $Me_3Si$ (TMS) groups of 2,2',6,6'-tetraisopropyl-4,4'-bis((trimethylsilyl)ethynyl) azobenzene according to a classical procedure.

The method for synthesizing the sterically hindered 2,2', 6,6'-tetraisopropyl-4,4'-diethynylazobenzene comprises: dissolving 2,2',6,6'-tetraisopropyl-4,4'-bis((trimethylsilyl) ethynyl)azobenzene in a methanol and tetrahydrofuran (THF) mixture to obtain a reaction mixture; adding potassium carbonate to the reaction mixture; evaporating the methanol and tetrahydrofuran (THF) from the mixture to obtain a crude residue; dissolving the crude residue in a mixture of $CH_2Cl_2$ and water to obtain an organic layer; extracting and drying the organic layer; removing the mixture of $CH_2Cl_2$ and water; and obtaining the sterically hindered 2,2',6,6'-tetraisopropyl-4,4'-diethynylazobenzene.

This synthetic scheme can be seen by referring to Scheme 1.

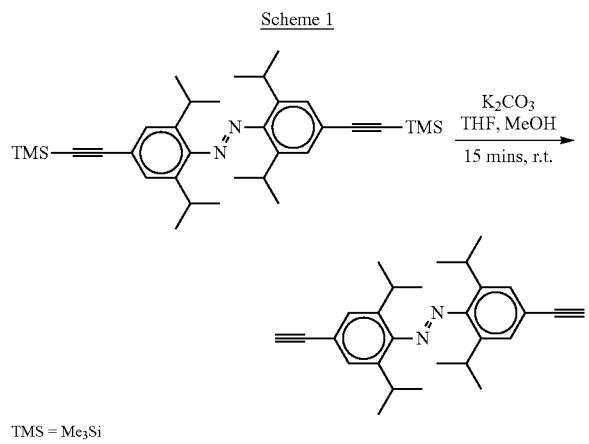

Scheme 1

TMS = Me$_3$Si

In another embodiment of the present production methods, the potassium carbonate may be added in excess.

In a further embodiment of the present production methods, the methanol and tetrahydrofuran (THF) mixture may be evaporated under vacuum.

In an embodiment of the present production methods, the organic layer may be extracted three times using CH$_2$Cl$_2$.

In further embodiments of the present production methods, the organic layer may be dried over MgSO$_4$.

In another embodiment of the present production methods, the CH$_2$Cl$_2$ may be removed in vacuo.

In an additional embodiment of the present production methods, the sterically hindered 2,2',6,6'-tetraisopropyl-4,4'-diethynylazobenzene may be obtained as an orange solid.

The following examples relate to various methods of manufacturing the specific compounds and application of the same, as described herein. All compound numbers expressed herein are with reference to the synthetic pathway figures shown above.

EXAMPLES

Example 1

Preparation of 2,2',6,6'-tetraisopropyl-4,4'-diethynylazobenzene 2,2',6,6'-Tetraisopropyl-4,4'-bis((trimethylsilyl)ethynyl) azobenzene (1.0 mmol) was dissolved in a methanol/THF mixture (10 ml/10 ml) and excess potassium carbonate (346 mg, 2.5 mmol, 2.5 eq.) was added. The completeness of the reaction was controlled via thin layer chromatography (TLC) (1 hour). After full conversion, the solvent was evaporated under vacuum. The crude residue was taken up in a mixture of CH$_2$Cl$_2$ and distilled water and the organic layer was extracted three times with CH$_2$Cl$_2$. The combined organic layers were dried over MgSO$_4$, and the solvent was removed in vacuo to provide the desired 2,2',6,6'-tetraisopropyl-4,4'-diethynylazobenzene as an orange solid.

Figure 2:
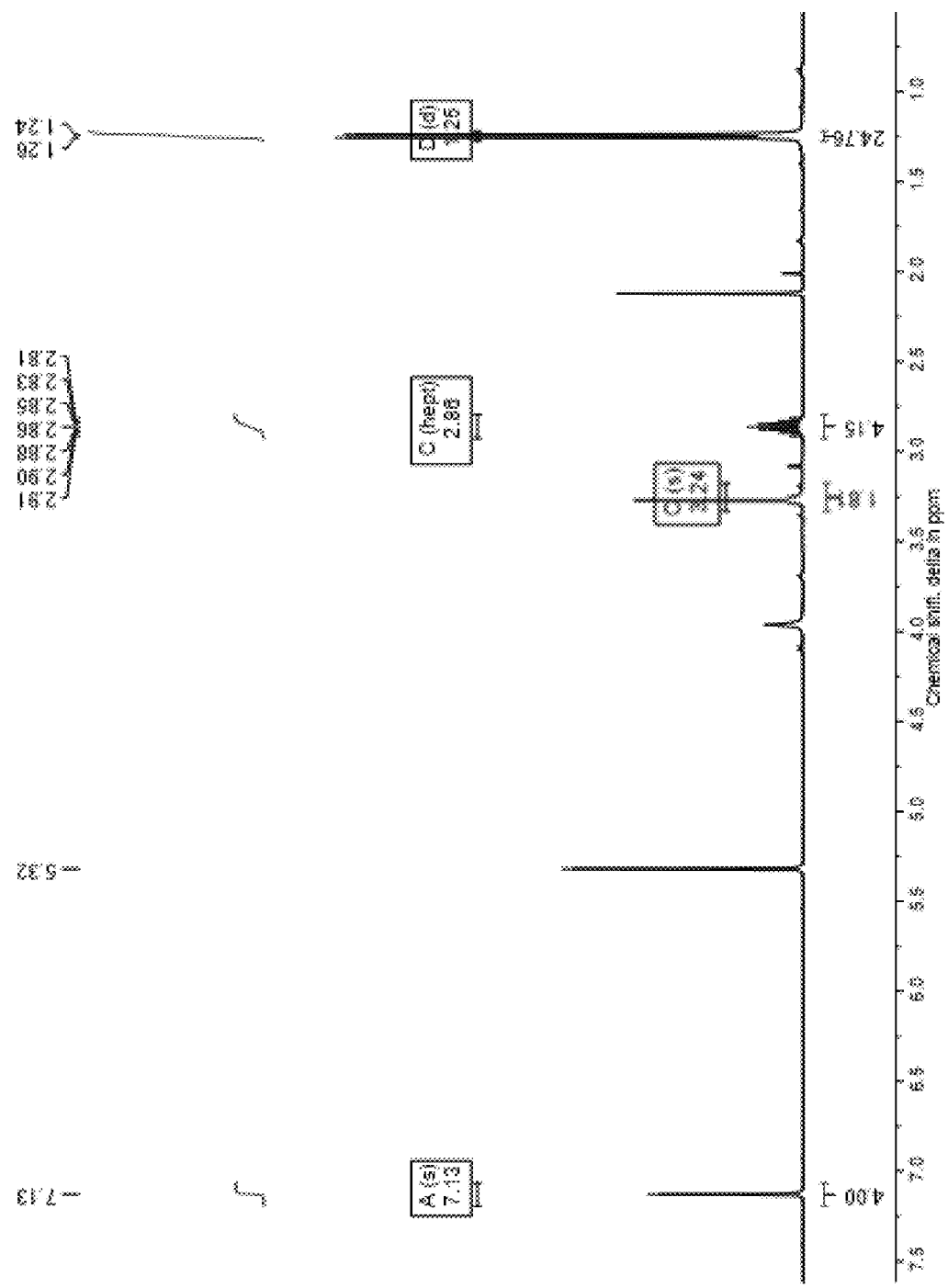
FIG. 2 shows the ¹H-NMR spectrum (400 MHz, CD₂Cl₂) of 2,2',6,6'-tetraisopropyl-4,4'-diethynylazobenzene.

Characterization of the prepared compound was determined using $^1$H-NMR (400 MHz, CD$_2$Cl$_2$): δ 7.12 (s, 4H, H(1)), 2.87 (hept, 4H, 3J=6.8 Hz, CH(CH$_3$)$_2$), 1.23 (d, 24H, 3J=6.7 Hz, (CH$_3$)$_2$CH), 3.25 (s, 2H, 2HC≡C) ppm, as shown in FIG. 2.

Elemental analysis for C$_{28}$H$_{34}$N$_2$: C: 84.37; H: 8.60; N: 7.03. Found: C: 83.96; H: 8.53; N: 7.12%.

UV-Vis (λmax (nm), ε(M−1·cm$^{-1}$)): 262 (1.5·10$^4$), 312 (1.8·10$^4$), 478 (1.9·10$^3$).

The identity of this novel sterically hindrance compound follows the correct numbers and integrations of its $^1$H-NMR data. The $^1$H-NMR spectrum showed a singlet of the four aromatic equivalent protons at ==7.13 ppm, another singlet observed at δ=3.24 ppm for the two-equivalent terminal ethynyl protons and classical heptet at δ=2.86 ppm and doublet at δ=1.25 ppm for the methine CH(CH$_3$)$_2$ and methyl (CH$_3$)$_2$CH protons of the four equivalent.

Example 2

Experimentation: Photo switchable cis- and trans-isomerization

The reversible conversion between the two trans- and cis-configurations of azoarylenes is highly controlled by irradiation of electromagnetic radiation. The most stable, trans-configuration can be converted to the less stable, cis-configuration using a UV wavelength of 340-380 nm. Visible illumination on the other hand at wavelength of 450-480 nm converts the azoarylene back to the trans-form as depicted in the sole figure. The two reversible azoarylene configurations are interchangeable by excitation of S$_0$→S$_1$ (assigned to the n→π* transition) or S$_0$→S$_2$ (corresponding to the π→π* transition). The S$_0$→S$_2$ excitation in trans-configuration exhibits a strong absorption in the UV-regime at 312 nm, while S$_0$→S$_1$ excitation exhibits a much weaker absorption band in the visible (Vis) at 478 nm. On the other hand, S$_0$→S$_2$ excitation of cis-azoarylene is relatively weaker than that of the trans form at about 280 nm, and S$_0$→S$_1$ excitation is relatively stronger than that of the trans form at about 450 nm.

Accordingly, the successfully prepared novel sterically hindered 2,2',6,6'-tetraisopropyl-4,4'-diethynylazobenzene with four bulky isopropyl groups on the ortho-positions shows a remarkably strong π→π* transition in the Visible (Vis) regime and underwent photo switchable of trans- and cis-isomers which is highly controlled by irradiation of electromagnetic radiation.

It is to be understood that the sterically 2,2',6,6'-tetraisopropyl-4,4'-diethynylazobenzene with four bulky isopropyl groups on the ortho-positions and compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A sterically hindered 2,2',6,6'-tetraisopropyl-4,4'-diethynylazobenzene complex having the formula I:

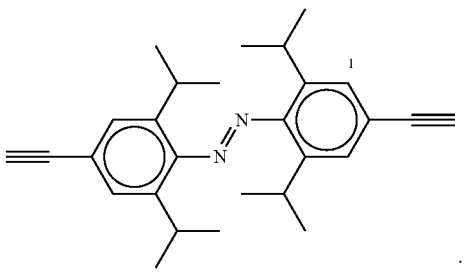

2. A method of making the sterically hindered 2,2',6,6'-tetraisopropyl-4,4'-diethynylazobenzene of claim 1, the method comprising:
   dissolving 2,2',6,6'-tetraisopropyl-4,4'-bis((trimethylsilyl)ethynyl)azobenzene, in a methanol and tetrahydrofuran (THF) mixture to obtain a reaction mixture;
   adding potassium carbonate to the reaction mixture;
   evaporating the methanol and tetrahydrofuran (THF) from the reaction mixture to obtain a crude residue;
   dissolving the crude residue in a mixture of $CH_2Cl_2$ and water to obtain an organic layer;
   extracting and drying the organic layer;
   removing the mixture of $CH_2Cl_2$ and water; and
   obtaining the sterically hindered 2,2',6,6'-tetraisopropyl-4,4'-diethynylazobenzene.

3. The method of making the sterically hindered 2,2',6,6'-tetraisopropyl-4,4'-diethynylazobenzene of claim 2, wherein the potassium carbonate is added in excess.

4. The method of making the sterically hindered 2,2',6,6'-tetraisopropyl-4,4'-diethynylazobenzene of claim 2, wherein the methanol and tetrahydrofuran (THF) mixture is evaporated under vacuum.

5. The method of making the sterically hindered 2,2',6,6'-tetraisopropyl-4,4'-diethynylazobenzene of claim 2, wherein the organic layer is extracted three times using $CH_2Cl_2$.

6. The method of making the sterically hindered 2,2',6,6'-tetraisopropyl-4,4'-diethynylazobenzene of claim 5, wherein the organic layer is dried over $MgSO_4$.

7. The method of making the sterically hindered 2,2',6,6'-tetraisopropyl-4,4'-diethynylazobenzene of claim 2, wherein the $CH_2Cl_2$ is removed in vacuo.

8. The method of making the sterically hindered 2,2',6,6'-tetraisopropyl-4,4'-diethynylazobenzene of claim 2, wherein the sterically hindered 2,2',6,6'-tetraisopropyl-4,4'-diethynylazobenzene is obtained as an orange solid.

* * * * *